United States Patent [19]

Harmer

[11] 4,240,747
[45] Dec. 23, 1980

[54] REFRACTIVE-INDEX RESPONSIVE LIGHT-SIGNAL SYSTEM

[75] Inventor: Alan L. Harmer, Geneva, Switzerland

[73] Assignee: Battelle Memorial Institute, Geneva, Switzerland

[21] Appl. No.: 81,351

[22] Filed: Oct. 3, 1979

Related U.S. Application Data

[63] Continuation-in-part of Ser. No. 919,981, Jun. 28, 1978, Pat. No. 4,187,025.

[51] Int. Cl.³ ............................................. G01N 21/41
[52] U.S. Cl. .................................. 356/133; 250/577; 250/227; 320/48
[58] Field of Search ................ 250/227, 577; 356/130, 356/132, 133, 135, 137; 350/96.15; 128/DIG. 13, 214 E; 320/48

[56] References Cited

U.S. PATENT DOCUMENTS 3,282,149  11/1966  Shaw et al. .......................... 356/130

FOREIGN PATENT DOCUMENTS 2130037  3/1972  France .

OTHER PUBLICATIONS

Armitage, Jr., J. D., "Measuring the Rate of Liquid-Bubbling", IBM Technical Disclosure Bulletin, vol. 6, No. 4, p. 71, Sep. 1963.

*Primary Examiner*—John K. Corbin
*Assistant Examiner*—Bruce Y. Arnold
*Attorney, Agent, or Firm*—Karl F. Ross

[57] ABSTRACT

A device for producing a light signal corresponding to the refractive index of a fluid medium comprises an elongated light-conducting body consisting of an input section and an output section connected to each other by an intermediate curved section adapted for immersion in said fluid. This curved section is provided with a plurality of curvatures arranged successively and bent alternately in opposite directions, whereby light passing by refraction into said fluid undergoes a notably greater variation, as a function of the refractive index of said fluid medium, than can be obtained with a curved section bent in a simple direction. A light signal is thus provided with a high sensitivity. The complex-curved, preferably Ω-shaped, section can be enclosed in an envelope composed in part of filter material.

12 Claims, 12 Drawing Figures

REFRACTIVE-INDEX RESPONSIVE LIGHT-SIGNAL SYSTEM

CROSS-REFERENCE TO RELATED APPLICATION

This application is a continuation-in-part of my copending application Ser. No. 919,981 filed 28 June 1978, now U.S. Pat No. 4,178,025.

FIELD OF THE INVENTION

My present invention relates to a device or system for providing a light signal representing the refractive index of a liquid.

BACKGROUND OF THE INVENTION

In many processes, it is required to detect changes of the state of a fluid medium, which may be either discontinuous changes of the state of this fluid (for example presence or absence of liquid) or continuous changes in the physical or chemical properties of this fluid (for example the concentration of a solution or of one of the constituents of a composite fluid, or temperature variations of a fluid). Such detection may be used for various applications such as carrying out measurements, control or testing operations. and regulation.

It has already been proposed, when a correlation exists between the characteristics of the fluid medium and its refractive index, to detect the changes in these characteristics by detecting variations of this refractive index by means of various optical methods. Most of these optical methods are based on exploiting the reflection and refraction phenomena which occur near the critical angle. They essentially consist in transmitting light through a transparent light-conducting structure immersed in the fluid medium, so that light undergoes multiple internal reflections on the walls of the structure. The determination of the intensity of the light thus transmitted by multiple reflections and the sudden variations of this intensity near the critical angle thus permits the refractive index of the fluid to be determined.

To make continuous refractive-index measurements there are, for example, devices of the type consisting of a straight transparent rod with an opto-mechanical system at one end for injecting a pencil of light into the rod with a well-defined angle of incidence, and with a photo-electric detector at its other end for measuring the intensity of the light thus transmitted through the rod by multiple internal reflections with a well-defined angle of incidence. When the rod is immersed in the fluid medium to be measured, the angle of incidence of the pencil of light injected into the rod is then made to decrease continuously while observing the transmitted-light intensity; the sudden drop in intensity which occurs when the angle of incidence of the multiple reflections exceeds the critical angle with respect to the fluid permits this critical angle to be determined and hence the refractive index of the fluid. Devices of this type, have the major drawback of being extremely complicated, given that they require, among other things, a relatively sophisticated light-injection system, since it must ensure both a parallel pencil of incident light by optical means, and a continuous variation of the angle of incidence of this pencil by mechanical means.

Moreover, various known devices for measuring liquid levels are of the type comprising a prism (or cone) placed on the bottom end of a transparent rod inserted into the vessel containing the liquid of which the level is to be determined, indication of this level being obtained by injecting light into the top end of the rod and by observing visually the light reflected by the prism back to the top end (this end is illuminated by reflecting light in the absence of liquid at the level of the prism, and becomes dark in the opposite case).

Devices of this sort have a certain number of drawbacks: firstly the small number of reflections which occur (simple or double reflection) only allows a low light contrast to be obtained, while the light-transmission factor remains relatively low; the structure of such devices has moreover proved relatively complicated. Above all, these devices exhibit the major drawback of being able to function in only two different fluid states on account of the fixed incidence of light, so that they are hardly suitable for carrying out continuous index measurements and their use thereby remains limited almost exclusively to the detection of changes of state such as level indication.

In order to remedy the above-mentioned drawbacks, it has further been proposed to use devices consisting of simple transparent rods comprising an intermediate U-shaped curved section adapted for immersion in the liquid to be tested, the refractive index of this fluid being determined by injection of light at one end of the rod and by observing the light transmitted to its other end. In such devices, the curved section of the rod results in the passage by refraction into the liquid of an amount of light which is found to be essentially a function of the refractive index of this liquid, so that the quantity of light transmitted to the other end of the rod constitutes a parameter which is characteristic of this refractive index (a device of this type is described for example in the article "A photo-electric refractometer" by E. Karrer and R. Orr—*Journal of the Optical Society of America*—Volume 36, No. 1—pages 42 to 46—January 1946). Such devices appear a priori to be particularly advantageous by virtue of their great simplicity and low cost, as well as the fact that they may be used in principle for the detection of both discontinuous and continuous changes in the characteristics of the liquid to be tested. However, these devices have the major drawback of having a very low sensitivity, so that their use as refractometers is quite limited (because of their inability to detect slight variations of the refractive index of the liquid to be tested), while even their use as simple liquid-level indicators is found to be far from satisfactory (because of the low contrast which can be measured).

It has been proposed more recently to provide different variants of these devices consisting of curved transparent rods, but none of these variants has led to a notable improvement of their sensitivity. Thus, for example, it has been proposed to replace the U-shpaed rod by a rod with a curvature of at least 360° (U.S. Pat. No 3,282,149), but this simply serves to linearize the measurement, without notably changing the sensitivity. It has also been proposed, for example, to replace the transparent rod by a curved optical fiber (French Pat. No. 2,130,037) essentially in order to achieve a miniaturization of the equipment, but this mere replacement also has practically no effect on the sensitivity.

OBJECTS OF THE INVENTION

The present invention has the object of avoiding the above-mentioned drawbacks by providing a simple device which has a notably increased sensitivity and can detect both discontinuous changes of state of a fluid and continuous variations of various characteristics of this fluid, which are linked to its refractive index.

Another object of my present invention is to provide a device or system responsive to refractive index of a liquid and which represents an improvement over the system of my copending application Ser. No. 919,981 now U.S. Pat. No. 4,187,025.

Yet another object of this invention is to provide a system wherein the sensor is less susceptible to problems involved in working with suspensions.

SUMMARY OF THE INVENTION

As described in the above-identified application, the present invention provides a device for producing a light signal corresponding to the refractive index of a fluid, comprising an elongated light-conducting body consisting of an input section and an output section connected to each other by an intermediate curved section adapted for immersion in the fluid, so that when light is injected into the free end of the input section, the passage of light by refraction into the fluid is a function of the refractive index of the fluid, and the light emerging at the free end of the output section provides a light signal corresponding to the refractive index of the fluid. The device has an intermediate curved section comprising a plurality of curvatures arranged successively so as to be alternately bent in opposite directions to one another, whereby the curvatures together provide passage by refraction into said fluid of an amount of light which varies as a function of the refractive index of the fluid. This variation is notably higher than can be obtained with a curved section bent in a single direction to thereby provide said light signal with a high sensitivity.

The device of the present invention can be used for detecting the presence of absence of said fluid, or for measuring a characteristic linked to the refractive index of said fluid.

In the present description, the expressions "elongated light-conducting body" or "light guide" are understood to cover any elongated body capable of conveying light by multiple internal reflections. This encompasses, more particularly, light guides consisting of a transparent rod or of an optical fiber (both being formed so as to comprise an intermediate curved section having the desired profile).

It may thus be seen that the essential characteristic of the device according to the invention resides in the use of a light guide comprising an intermediate curved section or several (at last two) alternating curvatures. Such a structure with alternating curvatures provides the major advantage of imparting to the device of the invention a particularly high sensitivity (the degree of sensitivity of such structure can be determined by the variation of the refractive index of the fluid to be measured), and in any case notably higher than that which can be obtained with a structure with a single curvature (whether it be U-shaped or with a curvature of at least 360°).

The intermediate section with alternating curvatures of the light guide constituting the device according to the present invention may be given various forms, so long as the different curvatures of this intermediate section remain successively arranged in such a manner that each of these curvatures be always bent in a direction opposite to adjacent curvatures. Among the possible forms which may be envisaged, one may use a structure with a double curvature, wherein the last curvature is bent in an opposite direction to the first curvature, or with a triple curvature wherein the middle curvature is bent in an opposite direction to the first and last curvatures, or else a structure having an even greater number of curvatures. In all of the above-mentioned structures, the different curvatures may moreover be mutually connected by intermediate straight portions, or on the other hand be directly adjoining (directly connected without being spearated from each other by straight portions). In the case of curvatures connected together by means of straight portions, these straight portions will moreover be advantageously chosen so that their length remains relatively small with respect to the dimensions of the curvatures to which they are connected.

In such structures with alternating curvatures as defined above, each of the curvatures may moreover assume any shape, provided it be sufficiently pronounced. Thus, I may choose curvatures having a constant radius in the form of an arc of a circle, which may moreover have various lengths such as quarter-circle, half-circle or full circle, or on the other hand curvatures with a variable radius, which can either increase or decrease progressively. The radius of curvature R of the different curved portions will advantageously be chosen small in relation to the transverse dimensions of the light guide, and to thereby provide a notable effect (the effect due to the curvatures being greater for smaller radii of curvature). This radius of curvature of the different alternating curvatures will preferably be chosen, for a given cylindrical light guide of a radius r, so that the ratio R/r lies between about 3 and 5.

In the case of a light guide consisting of a simple transparent rod, this rod can be made of any appropriate transparent material. When the device is used to determine continuous index variations, this material must have a higher index of refraction than that of the measured liquid; when, however, the device is used as a level indicator, it may have any index of refraction, greater or less than that of the measured liquid. As possible transparent materials, one may envisage using plastic materials such as polystyrene (n=1.59), polymethylmethacrylate (n=1.49), etc. or glasses such as silica (n=1.458), borosilicate glasses (typical n=1.5), lead glasses (typical n=1.7), fluoride glasses (typical n=1.35), etc.

The size of the cross-section of the light-conducting rod with alternating curvatures according to the invention is of little importance as such, since it is the ratio R/r of the radius of curvature R of the different curvatures to the radius r of the rod which is in fact the determining factor for achieving the desired effect. Thus one can in practice use rods with either a very small cross-section or a relatively large cross-section and then simply adapt in each case each radius of curvature to the selected cross-section of the rod. It is moreover not essential that this cross-section be circular, and one may very well envisage using rods with a square, hexagonal, elliptic cross-section (in such a case the radius of curvature R must be sufficiently small with respect to the cross-sectional rod dimension in the plane of curvature).

In the case of a light guide consisting of an optical fiber, one can in principle carry out the invention with any appropriate type of fiber (these fibers may, moreover, be made of glass-based or plastic-based materials). However, it is particularly advantageous to choose more especially so-called step-index fibers. When optical fibers are used, the presence of a cladding around the light-conducting core presents the additional advantage of preventing, in non-curved parts of the fiber, any risk of a disturbing influence of a parasitic medium which may possibly be present. As regards the curved portions of these fibers, one may moreover envisage either to strip them completely of their cladding, so as to permit direct contact of the central core with the fluid medium to be tested, or on the other hand to leave them completely protected by their cladding. The results obtained have in fact shown that the presence of a cladding around the curved portions of the fiber does not fundamentally modify the phenomena of light loss by refraction on passage through these curved portions; the presence of this cladding as a matter of fact leads to only a slight decrease of contrast, the intensity of the transmitted light always remaining characteristic of the surrounding fluid medium to be tested. In this last case, however, i.e. with cladded portions, fibers have a cladding of relatively small thickness are preferably used.

In the present description, the term "angle of incidence of a light ray on a surface" will moreover be used according to its usual definition, namely the angle which this incident light ray makes with respect to the normal to this surface. According to this definition, an increase of obliquity of the incident light ray with respect to the surface is equivalent to a decrease of its angle of incidence.

The definition of two parameters will finally be given which are often used in the following description, in order to explain better the effects provided by the curved section of the device according to the invention, namely, the "coefficient of transmission in air" and the "contrast coefficient" of the device. Thus, in this respect, $I_o$ will be the light intensity injected at the input of the curved light guide, $I_{ta}$ the light intensity transmitted by this guide when the medium surrounding the curved section is air, and $I_{tl}$ the light intensity transmitted by this guide when the medium surrounding the curved section is a liquid with an index of refraction n (this liquid may moreover be the liquid to be tested or a reference liquid). The "coefficient of transmission in air" is the ratio $I_{ta}/I_o$ of the light intensity $I_{ta}$ transmitted by the guide in presence of air to the light intensity $I_o$ injected into the guide (this coefficient permitting to define in a fashion the light losses by refraction in presence of air), and "contrast" or "contrast coefficient" is the ratio $I_{ta}/I_{tl}$ of the light intensity $I_{ta}$ transmitted in presence of air to the light intensity $I_{tl}$ transmitted in the presence of liquid. According to this last definition, the "sensitivity" of the device may also be defined as being represented by the magnitude of the variation of contrast obtained for a predetermined variation of index (sensitivity corresponding to the slope of the curves in the diagram of FIG. 6).

BRIEF DESCRIPTION OF THE DRAWING

The accompanying drawing illustrates schematically several embodiments as well as variants of the present invention. In the drawing.

SPECIFIC DESCRIPTION AND EXAMPLES

Figures 1A, 1B, 2:
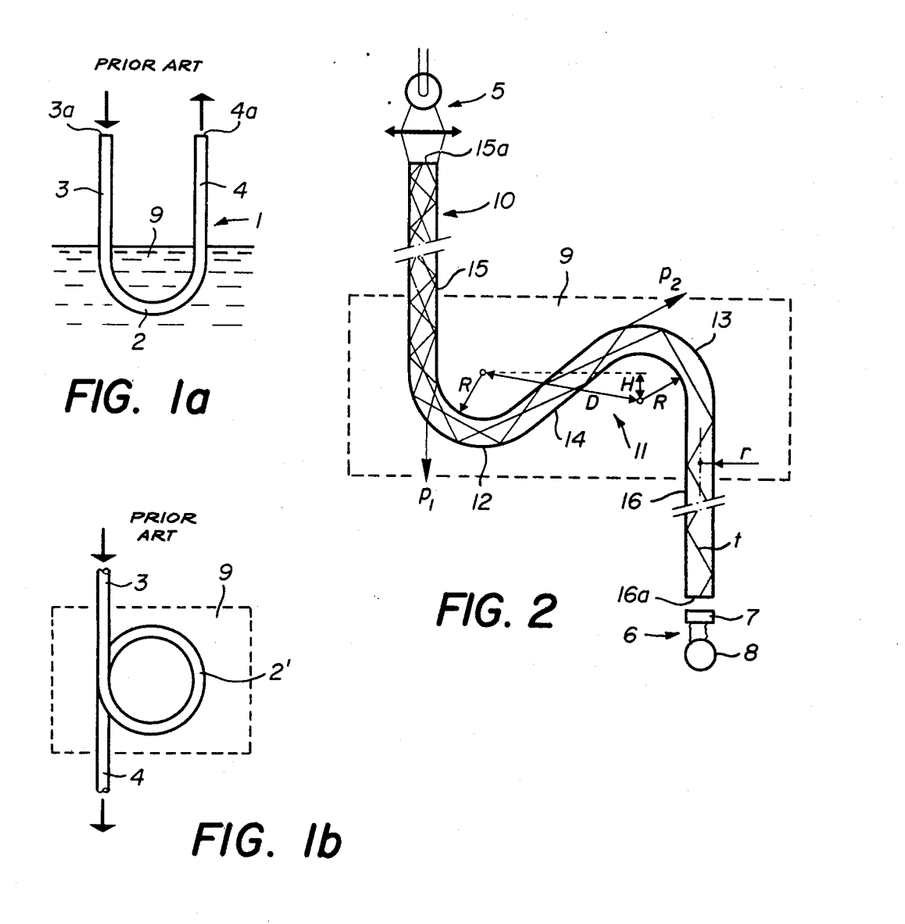
FIGS. 1a and 1b are schematic, longitudinal sectional views illustrating two devices known from the prior art.
FIG. 2 is a schematic, longitudinal sectional view illustrating a first embodiment of the device according to the invention.

FIGS. 1a and 1b illustrate as an example two devices known from the prior art. These two first illustrations serve to explain the main differences which exist between the known devices and the different embodiments of the device according to the invention which will be described hereinafter. The device represented in FIG. 1a comprises a transparent U-shaped rod 1 having a curved section 2 of semi-circular form which is prolonged at each of its ends by straight sections 3 and 4.

The free end 3a of the straight section 3 serves to inject light into the rod 1, while the free end 4a of the other straight section 4 serves to detect the light transmitted through the rod 1 (injection and output of light schematized by arrows in the drawing).

The curved section 2 being immersed in liquid 9 to be tested, the amount of light emerging at the extremity 4a is found to be a function of the index of refraction of the liquid 9. The device represented in FIG. 1b is analogous to that of FIG. 1a, apart from the fact that the curved section 2 of semi-circular form is replaced here by a section 2' which is looped through 360°.

FIG. 2 illustrates a first embodiment of the device according to the invention, which comprises a light guide consisting of a simple transparent rod provided with two alternating curvatures bent in opposite directions. The device represented in this Figure has a rod 10 made of a transparent material, which consists of an intermediate curved, S-shaped section 11 and of two straight sections 15 and 16 extending substantially vertically from each of the ends of this curved section 11. The straight sections 15 and 16 are intended to respectively serve as an input section and an output section for the rod 10.

The S-shaped section 11 consists of two successive curved portions 12 and 13 both in the form of an arc of a circle connected to each other by an intermediate straight portion 14, these two curved portions 12 and 13 being moreover arranged in a substantially symmetrical manner with respect to each other, while being bent in opposite directions to each other. The transparent rod 10 has a circular cross-section of radius r, while the curved portions 12 and 13 have a constant radius of curvature R.

In the vicinity of the plane end-face 15a of the input section 15 there is arranged a light source 5 adapted to inject light into the transparent rod 10, while in the vicinity of the end-face 16a of the output section 16 there is arranged a detection system 6 adapted to determine the light intensity transmitted by the rod 10. For example, this detection system 6 may consist of a photoelectrical detector 7 electrically connected to a measurement and/or display device 8. The curved section of this device is adapted to be immersed in a liquid 9 with a refractive index n, of which one of the characteristics linked to this refractive index is to be determined. The transparent material of the rod 10 is chosen so as to have a refractive index $n_1$ greater than the refractive index n of the liquid to be tested.

The geometry of the structure with double curvature which has just been described is essentially controlled by three parameters: the radius of curvature R of each of the curved portions 12 and 13 (or else the ratio R/r where r is the radius of the rod), the distance D separating the centers of curvature of each of these curved positions, and their offset H. The radius of curvature R will preferably be chosen relatively small, as a function of r, so as to ensure optimum increase of the contrast and sensitivity of the device. Advantageously the ratio R/r lies between about 3 and 5. Also for the same reasons, it is moreover of interest to maintain the distance D in the vicinity of the minimum permitted by the radius of curvature (that is, about 2R+2r). Always for the same reasons of contrast and sensitivity, it is finally of interest to choose the offset H to be substantially nil or slightly positive (i.e. with an overlap as represented in FIG. 2).

The operation of the device just described may be explained as follows:

The curved section 11 of this device being immersed in the liquid 9 to be tested, light is injected into the transparent rod 10 by means of the source 5. The light delivered by this source 5 may have any divergence, given that the amount of light effectively trapped by the transparent rod 10 only depends on the "numerical aperture" of this rod and not on the divergence of the incident beam. It is known that the only incident rays which will be trapped within the rod are those which strike its wall at an angle of incidence greater than its critical angle with respect to the surrounding medium (air), the other rays with a smaller angle of incidence being refracted out of the straight section 15. The light so trapped within the transparent rod 10 is then transmitted by multiple internal reflections through the straight section 15, until it arrives in the curved section 11 immersed in the liquid 9 to be tested, except for certain rays escaping earlier from section 15 by reason of the change in the external refractive index at the point of immersion.

The first curvature 12 of this curved section 11 has the effect of modifying the incidence of the rays which strike its walls, while causing in particular a reduction of the angle of incidence of those rays which come to strike its outer surface (this reduction of the angle of incidence being moreover a function of the magnitude of the curvature), so that incident rays whose angle exceeds the critical angle with respect to the surrounding liquid 9 are then forced to pass by refraction into the liquid (behavior illustrated by the ray $p_1$ in the drawing). For a given curvature, this reduction of the incidence is nevertheless not identical for all the rays which arrive with the same incidence in this curved portion 12, since it depends on the depth at which these rays have been able to penetrate into this curved portion before striking its outer surface, so that only a part of the rays which arrive under the same incidence is liable to pass out of the rod 10 by refraction into the surrounding liquid. The proportion of rays which are liable to be refracted out into the surrounding liquid is evidently a function of the refractive index of this liquid, since the critical angle of total reflection depends on the index. The remaining part of the rays which have not escaped from the rod at this first incidence on the curved portion is then totally reflected into the interior of the rod and transmitted by successive internal reflections to the second curvature 13 (it can be easily shown that it is the first incidence on the curved portion which determines the possibility of passage of the rays into the surrounding medium; a ray totally reflected after this first incidence is then subsequently reflected along the first curvature at constant angles of incidence, equal to that of the first incidence, which no longer allows it to leave the rod up to the next curvature).

The rays totally reflected by the first curvature 12, which tend to be transmitted by multiple reflections along the radially outer surface of this first curvature, then have to arrive in the second curvature 13, thanks to the inversion of the latter, so that a major part of these rays comes to strike its wall under an extremely low angle of incidence and is thereby forced to pass by refraction into the surrounding medium (behavior illustrated by the ray $p_2$ in the drawing). The proportion of the rays forced to pass by refraction into the surrounding liquid is evidently a function of the refractive index of this liquid, given that the critical angle of total reflection here also depends on this index. The remaining part of the rays which has not escaped from the rod during this first incidence on the second curvature 13 is totally reflected into the interior of the rod (the subsequent incidences in fact occurring at angles equal to the of the first incidence), and hence is transmitted by successive internal reflections up to its other end 16a (behavior illustrated by the ray t in the drawing).

Consequently, the intensity of the light thus emerging at the other end 16a of the rod, which is substantially equal to the intensity of the light injected into the rod minus the losses due to refraction occurring primarily in the curved portions 12 and 13 (aside from the absorption losses in the rod), is thus likewise a function of the refractive index of the medium surrounding the curved section. This transmitted light intensity hence provides a light signal which is characteristic of and corresponds to the refractive index of the medium surrounding the curved section of the rod.

The light signal thus produced by the device just described nevertheless differs essentially from that produced by the known devices of FIGS. 1a and 1b (although in both cases characteristic of the refractive index of the fluid to be tested) by the fact that it exhibits here a much higher sensitivity, this quite unexpected result being due to the presence of the second curvature 13, bent in the opposite direction to the first curvature 12, which has so to speak an amplifying action on the effects obtained during passage along this first curvature. This second curvature 13 bent in an opposite direction in fact permits one to multiply the effects obtained during passage of first curvature 12, this being due to the fact that the rays penetrating into this second curvature have already had their path sufficiently modified during their passage in the first curvature so that they must strike the second curvature with a great obliquity (small incident angle), which thus obliges the greater part of these rays to leave the rod by refraction at the level of this second curvature (such great obliquity is on the other hand impossible to achieve during penetration into the first curvature, owing to the limited "numerical aperture" of the input section 15 of the transparent rod).

That the device according to the invention allows a particularly high sensitivity to be achieved (and hence a high contrast) will be clearly demonstrated in the examples given further on.

It has been said in the foregoing that it is the first incidence at the entry of the first curvature which determines the refraction losses in this curvature; the rays totally reflected after this first incidence then tend to be transmitted by multiple reflections along the radially outer surface of the curvature under small and constant angles of incidence. It may thus be seen that it is unnecessary to increase the length of this curvature by causing it to undergo several turns in the same direction (case of the known device of FIG. 1b), given that such a measure would only result in reducing the light transmission (because of increased absorption in the transparent material) without in any way increasing the contrast and sensitivity. The only measure found to be effective for notably increasing contrast and sensitivity is that according to the invention, namely, of providing the first curvature followed by at least one second curvature bent in the opposite direction.

The qualitative explanations given above with regard to the effect of the curvatures are in fact only approximate and apply essentially to the meridional rays (i.e. rays intersecting the axis of the light guide), whereas the skew rays which do not intersect this axis nevertheless convey a major part of the light injected into the transparent rod. Yet, it is practically impossible to carry out a theoretical global analysis of the phenomenon, on account of the highly complex behavior of these skew rays. One could attempt a more complete theoretical approach, taking into account the behavior of these skew rays, by providing a mathematical treatment based on an analysis of the different modes of propagation within the transparent rod. However, such a treatment is already difficult to establish in the case of a single curvature, subjected to the penetration of a uniformly distributed radiation, and appears to be very difficult or impossible in the case of a second alternating curvature, in view of the non-uniformity of the spatial distribution of the light entering the second curvature (non-uniformity due to the effect of the first curvature which entails a concentration of light energy near the radially outer surface of this curvature).

The qualitative explanations given above, although only approximate, are nevertheless amply corroborated in practice by the different experimental results obtained by measurement of the transmitted light intensity (which takes into account both the skew rays and the meridional rays), as is clearly shown by the examples described below.

Figure 3:
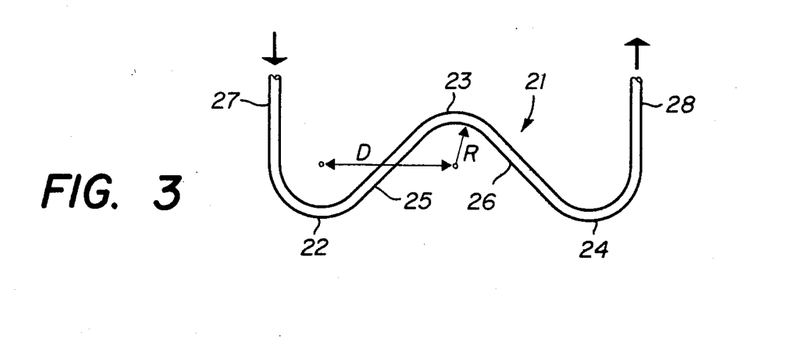
FIG. 3 is a partial longitudinal sectional view illustrating a variant of this first embodiment.

FIG. 3 illustrates a variant of the described embodiment according to FIG. 2, which consists of a transparent rod 21 having three alternating curvatures. The rod 21 in the general shape of a W, shown in this Figure consists of three curved portions 22, 23 and 24 each in the form of an arc of a circle respectively connected to one another by two intermediate portions 25 and 26 (the curved middle portion 23 being bent in the opposite direction to the outer curvatures 22 and 24), the free ends of the outer curvatures 22 and 24 moreover being prolonged by straight portions 27 and 28.

Figure 4:
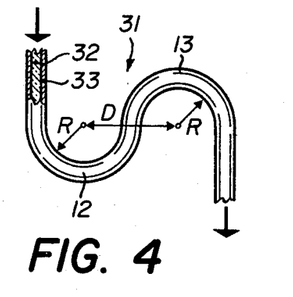
FIG. 4 is a view similar to that of FIG. 3, illustrating a second embodiment.

FIG. 4 illustrates a second embodiment of the device according to the invention, which comprises an optical fiber with a double curvature. This structure is similar to that of FIG. 2, but the transparent rod 10 made of a single material is replaced here by an optical fiber 31, which is composed of a central core 32 surrounded by a cladding of slight thickness 33 along the entire length of the fiber. The geometry of this structure moreover differs from that represented by FIG. 2 in that the curvatures 12 and 13 are here directly adjoining (i.e. contiguous with no intermediate portion between the curvatures) and are of semi-circular form, while the offset H is moreover here chosen equal to zero.

Figure 5:
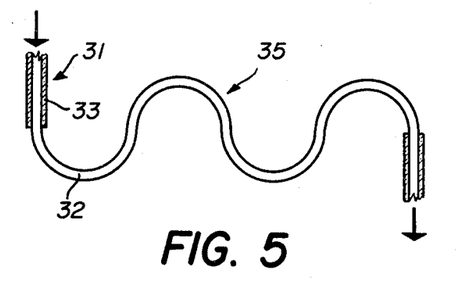
FIG. 5 is a view similar to that of FIG. 4, illustrating a variant of this second embodiment.

FIG. 5 illustrates a variant of the device of FIG. 4, wherein the optical fiber 31 is provided with a curved section 35 comprising four alternating curvatures (instead of two as in FIG. 4), this curved section 35 moreover being completely stripped of the cladding 33 (core 32 laid bare).

EXAMPLE 1

This example serves to establish a comparison between results obtained with the device according to the invention and with devices known from the prior art, so as to show their essential differences.

One uses as starting material a plastic optical fiber PS/PMMA of 1.5 mm external diameter, consisting of a central core of 1.03 mm diameter made of polystyrene (index equal to 1.59) and of a cladding of 60 micron thickness made of polymethylmethacrylate (index equal to 1.49). This fiber is used to make the following structures (all these structures keeping their cladding in the curved portions):

(a) A first structure comprising a simple curvature of 180° (similar geometry to that of FIG. 1a), which presents a radius of curvature R equal to 1.75 mm;

(b) A second structure comprising a single curvature of 360° (similar geometry to that of FIG. 1b), whose radius of curvature is also equal to 1.75 mm;

(c) A third structure comprising a double alternating curvature (similar geometry to that to FIG. 2), with the following parameters: R equal to 1.75 mm, D equal 4.65 mm (2R+2r), and H equal to +0.97 mm; and (d) A fourth structure comprising a quadruple alternating curved section (similar geometry to that of FIG. 5), with the following parameters: R equal to 1.75 mm, D equal to 4.65 mm (2R+2r), and H substantially nil.

The above-mentioned structures are made for example by heating the fiber to a temperature between 100° and 200° C., and by forming the fiber thus heated around cylindrical mandrels of appropriate dimensions (having in particular an external radius equal to 1.75 mm).

Light transmission through each of these structures is then measured by means of a source consisting of a 150 W quartz-iodine lamp and a silicon photodiode detector having a spectral response lying between 400 and 950 nm with a peak at 700 nm. A series of measurements is carried out by immersing said structure in liquids of different known refractive indices (ranging from 1.33 to 1.47). The results thus obtained are given in the diagram of FIG. 7, which illustrates the variation of the coefficient of contrast $\Gamma$ as a function of the refractive index n of the liquid in which the different above-mentioned structures are immersed. The curves A and B in FIG. 6 correspond respectively to measurements with the first and second structures known from the prior art, whereas the curves C and D relate to the third and fourth structures according to the invention (the curves A and B being practically indistinguishable at the scale of the drawing). This diagram clearly illustrates not only the superiority of the performance (both with regard to the contrast and to the sensitivity) of the structures according to the invention with respect to those known in the prior art, but also more particularly the quite unexpected synergetic effect provided by the alternating curvatures according to the invention; these alternating curvatures indeed allow one to obtain performances which are greatly magnified with respect to the single curvatures used in the prior art, and moreover far greater than a simply doubled or quadrupled performance.

EXAMPLE 2

This example serves to illustrate how light intensity transmitted by the device according to the invention may vary as a function of the magnitude of the curvatures of the light-conducting rod.

As starting material one uses optical fibers (commercially available under the name of CROFON from the Company Dupont de Nemours) of 1 nm external diameter, consisting of a core made of a first plastic material with an index n equal to 1.49 (polymethylmethacrylate) and a cladding made of a second plastic material with an index n equal to 1.39 (thickness of cladding less than 50 microns).

Three optical-fiber structures are made with double curvature which are identical to those illustrated in FIG. 4 namely, a structure having a distance D equal to (2R+2r) and a distance H equal to zero. These curvatures differ from each other in that a different radius of curvature R is chosen in each case, namely respectively 2 mm, 1.75 mm and 1.5 mm (D being then respectively equal to 5 mm, 4.5 mm and 4 mm). Each of these structures is respectively immersed in air and in a reference liquid with a refractive index equal to 1.39 (benzine), and one measures each time the light transmitted through these structures in the same way as before. The resulting measurements allow one to determine, for each of these structures, a contrast coefficient respectively equal to about 8, 18 and 75, as well as a coefficient of transmission in air respectively equal to 55%, 50% and 43%. It may thus be clearly seen that the contrast increases strongly as a function of the degree of curvature, this strong increase with regard to contrast being moreover accompanied by a relatively slight decrease of the coefficient of transmission in air.

The production by the device according to the invention of a light signal which is characteristic of the refractive index of the fluid in which it is immersed may be employed both for detecting discontinuous changes of state of this fluid and for determing different characteristics of this fluid linked to its refractive index (or continuous variations of these characteristics).

In the first of the applications just cited, the device according to the invention may be used particularly advantageously to detect the presence or absence of a fluid at a given place, and more particularly the height or level of the liquid in a given container, the different curvatures constituting the curved section of the light conductor being then disposed at the level to be detected. In this application as a level indicator, the device may be extremely simplified, given that it must only detect two different states: one may thus completely eliminate the system for detecting the transmitted light and replace it by a simple visual observation. The curvature of the curved portions may moreover be advantageously chosen so as to cause minimal losses of light in the absence of liquid, so that the observed end of the light conductor appears darker if the liquid is at the desired level or on the contrary becomes illuminated in the absence of liquid. One may also envisage eliminating the light source permanently mounted at the input end of the light conductor, and to replace it with a simple auxiliary light source (for example a portable lamp such as a flashlight) with which one would light this input end when one desires to verify the level. As regards this liquid-level detection, one may moreover envisage carrying out both a discrete detection (measurement of a single level) and a quasicontinuous detection (measurement of several levels within the same container, for example maximum and minimum levels), and installing a device at each of the levels to be detected.

Figure 7:
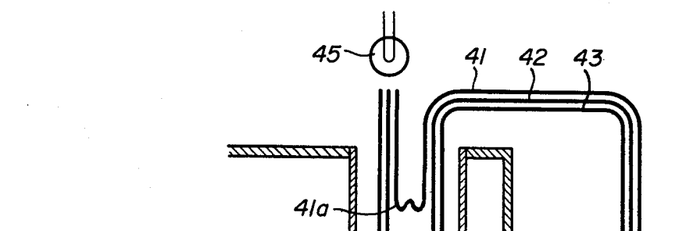
FIG. 7 is a longitudinal sectional view of an apparatus for the detection of a plurality of levels, using several devices according to the invention.

FIG. 7 illustrates an example of an apparatus for measuring three distinct level within a container 40 (maximum, middle and minimum levels). This apparatus consists of three optical fibers according to the invention, 41, 42 and 43, mounted within a tube 44 immersed in the container 40. These three optical fibers have curved sections 41a, 42a and 43a, in the form of a W arranged at the height of the levels to be measured. In this apparatus, light is injected into the input sections of the fibers by a single common source of light 45, while the indication of level is obtained by simple visual observation of the free ends of the output sections of these fibers. When the container is for example three-quarters full as shown in the drawing, only the output end of the fiber 41 will appear illuminated, while the ends of the two other fibers 42 and 43 will remain dark.

The device according to the invention has multiple applications as a level indicator. It can be used in the field of automobile (or aeronautic) instrumentation to detect levels such as that of a gasoline tank, of motor or transmission oil, of brake fluid, of battery electrolyte, of windshield-washer liquid, etc. The different output ends of the optical fibers used to detect these levels may for example be mounted on the dashboard of the vehicle. One may also consider using such a level indicator in many other fields, such as the storage of liquefied gases (where level measurements are generally difficult to carry out on account of fire hazards, low temperatures and a corrosive environment), storage tanks for chemical products, etc.

The device according to the invention may also be used as a refractometer, in order to measure either the refractive index of a fluid directly, or other characteristics of this fluid linked to its refractive index, such as the concentration of a solution, proportion of one of the constituents of a composite fluid, temperature of a liquefied fluid, etc. In such an application as a refractometer, the means for detection of the transmitted light may consist of an electric system comprising for example a phototransistor connected to a measurement device (which may be adapted so as to directly give the value of the characteristic to be measured), or on the other hand of a simple visual system based on the observation of the attenuation of the intensity or color change (which may possibly be compared with those of a control fiber).

Figure 6:
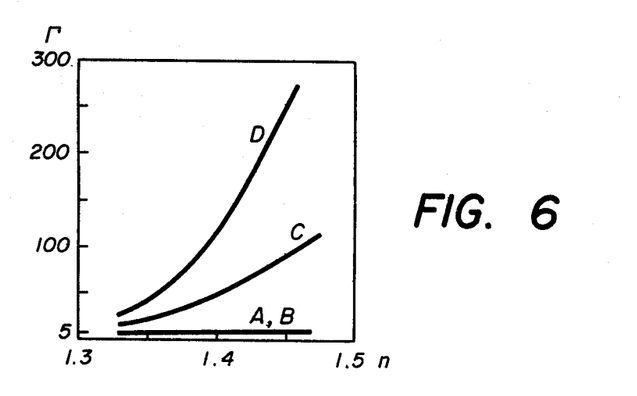
FIG. 6 is a diagram illustrating results obtained with a device according to the invention, as compared with those obtained with known devices of the prior art.

The fields of application of such a refractometer are manifold: chemical industry, medical field, instrumentation in general, automobile or aeronautic instrumentation, etc. In the field of automobile instrumentation, one may consider using this refractometer for applications such as determination of the state of charge of a lead-acid battery or determination of the concentration of an anti-freeze mixture. With regard to this first application to a battery, one can determine the state of the conventional lead-acid battery by measuring the variations of the refractive index of the electrolyte, this index falling from 1.378 at full charge to 1.348 when the battery is discharged; the diagram of FIG. 6 shows that this variation of index would correspond to a variation of the contrast coefficient from about 88 to 35 for the optical fiber corresponding to curve D (or a variation of the contrast coefficient from about 35 to 19 for the optical fiber corresponding to the curve C), which can be easily measured visually or electronically. As regards the second application to anti-freeze mixtures, it is moreover known that propylene glycol is increasingly replacing ethylene glycol which is now forbidden in numerous countries on account of its high toxicity: the determination of the percentage of ethylene glycol by means of a densitometer can unfortunately not be applied to propylene glycol, since its density is very close to that of water, so that the device according to the invention constitutes in this case a particularly advantageous alternative solution.

The device according to the invention has numerous advantages with respect to known level gauges or refractometers: simplicity both in its construction and operation, low cost, high contrast rendering it particularly attractive for use as a level indicator, and excellent sensitivity to refractive-index changes, making it particularly suitable as a high-performance refractometer.

Under certain conditions the aforedescribed apparatus according to the invention, which provides a luminous signal characteristic of the index of refraction of a liquid, may be disturbed by the presence in the liquid of solid particles in suspension which can deposit upon or contaminate the sensing portion of the device, namely, the complex-curved light pipe. This is particularly the case where such particles can progressively accumulate upon the sensing portion.

Contamination of this type is particularly significant in a variety of liquid media which originally contain solids in suspension or where solids tend to form with time.

A typical case is where the sensing device is immersed in the electrolyte of a conventional lead-acid storage battery or cell. Such electrolytes tend to be altered progressively in the course of time, at least in part, by the formation of an accidental suspension of particles which progressively separate from the battery plates and/or the vessel walls. Such particles include colloidal lead, lead sulphate and other impurities and are formed in particle sizes ranging down to about one micron.

To avoid interference with the measurements made with the device of the present invention by such particles, I provide a protective enclosure around the sensing portion of the light pipe and immersed in the liquid, at least part of this envelope or enclosure being composed of a filter material designed to prevent solid particles of the sizes concerned from depositing upon the sensing portion of the light pipe while freely passing the liquid.

Figure 8:
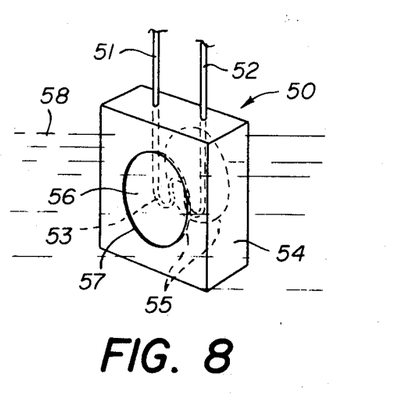
FIG. 8 is a schematic perspective view illustrating a third embodiment.

FIG. 8 shows an embodiment of the enclosure which is applicable in accordance with this feature of the invention, it being understood that this enclosure can be used with the sensing portions of the devices shown in and described with reference to FIGS. 2, 3, 4, 5, 7, and 9.

The sensing portion of the device is a fiber-optical unit 50 comprising an input stretch or section 51, an output stretch or section 52 and a complex-curved section 53, lying between the input and output sections and consisting of three curves generally in the form of an $\Omega$.

A parallelepipedal enclosure 54 sealingly surrounds the intermediate section 53 and consists of a material which is chemically inert to the liquid such as nylon or Delrin, the sealing being effected between the enclosure 54 and the portions of the optical fiber which pass through the walls thereof by a chemically inert adhesive such as an Araldite epoxy resin.

The two opposite major faces of the enclosure 54 are provided with circular openings or windows 55 in which thin disks 56 are mounted, these disks consisting of an appropriate filter material. These disks are held in place by collars 57, one of which is shown diagrammatically in the drawing. The sensing portion 53 of the fiber 50, provided with its protective enclosure 54, is shown to be immersed into a liquid 58 to be evaluated.

The filter disks are designed to permit free passage of the liquid 58 into and out of the enclosure 54 and thus into contact with the sensing portion 53 so as to permit, at the output stretch or section of the optical fiber, a luminous signal to develop which is a characteristic of the index of refraction of the liquid 58 (in accordance with the principles previously described), while preventing at least a major part of the solid particles in suspension in the liquid from reaching the sensing portion 53 and hence without disturbance of the measurement.

The filter material constituting the disks 56 can be any material capable of fulfilling the functions described above to the disk and, in addition, should be chemically inert to the liquid in which the enclosure is immersed.

Generally the filter material will represent a compromise between the need to exclude particles and the desire for full permeability to the liquid since measurement precision in liquids of changing index of refraction will depend upon the rate at which such changes are communicated to the liquid in contact with the sensing portion and hence the rate of diffusion through the filter.

A variety of commercial filter materials have been found to be satisfactory for most purposes, including glass-fiber filters such as the Whatman filters GF/A and Gf/C made from a fine mesh of borosilicate glass fibers without a bonding agent and of a thickness of about 0.25 mm which permit blockage of all particles having a particle size down to about one micron.

Alternatively, a Cambridge fiber-glass filter bonded with polyester resin and having a thickness of 1.5 mm can be used to block particles of a particle size down to 0.1 microns. Porous fritted-glass filters, such as Sovirel filters G1 and B2, may be used, these filters being made from sintered borosilicate glass frit and having a thickness of the order of 3 mm, permitting blockage of particles of a particle size down to 90–200 microns.

Other filter materials can, of course, be used and will generally be designed for the particular application. For example, when the device is used in a storage battery to continuously monitor the index of refraction of the electrolyte and hence the density or charging condition, the filter should enable the device to have a response time of the order of that which is introduced by the separators between the active electrolytes. The filters can then be formed from the same materials as such separators.

A typical material for this purpose is a PORVIC 1 polyvinyl chloride which is the material used as a separator in a Dagenite storage battery and which constitutes a sintered sheet with a fine-pore structure and a thickness of the order of 0.8 mm. Such filters can block particles down to a particle size of about 5 microns.

Another material suitable for this purpose is the polyester film or foil used for battery-separator purposes such as Yuasa separators YT 100B and Y3115 which have thicknesses, respectively, of the order of 0.17 mm and 0.10 mm but block particles of a particle size as low as about 0.1 microns, so that they are flexible and can be bent to different shapes and soldered for encapsulation.

The configuration of the protective enclosure shown in FIG. 8 can be varied, in accordance with the present invention, as desired for any particular purpose. For example, the entire protective enclosure can be composed of the filtering material or the enclosure can comprise a double thickness of the filtering material of which one layer is more distal from the sensing bends of the light pipe than another. In this case, the outermost filter can serve as a prefilter with the innermost filter serving as a final filter. The coarser particles can be trapped on the prefilter while the finer particles ae trapped on the final filter.

The enclosure can be constituted by filtering material applied directly on the sensing bends, thereby forming an especially compact device.

It should be noted further that an enclosure such as that shown at 54 is applicable not only to the complex-curved optical sensor shown in FIG. 8 or disclosed elsewhere in this application, but to any type of optical detector adapted to be immersed in a liquid medium which contains or may come to contain solid particles in suspension. Such a sensor can have a simple curve (single curve as in FIG. 1a) or may have a sensor portion formed by a prism or the like.

The protective enclosure of the present invention has, apart from its major advantage in preventing perturbations by contamination of the sensitive part of the optical detector, a number of other advantages which can serve to exclude environmental or ambient phenomena from affecting the results.

For example, the filtering enclosure reduces the effect of all kinds of oscillations upon the interface formed by the light pipe and the liquid, e.g. vibrations, vehicle movements and the like, and provides an optical signal free from parasitic fluctuations especially in the case in which the sensing portion of the device is only partially immersed in the liquid.

The enclosure also precludes parasitic fluctuations in the optical signal which may be caused by contact of gas bubbles with the sensor in cases in which such gas bubbles may form in the liquid.

When the filtering material is opaque, in accordance with another feature of the invention, it serves as an ambient light seal to eliminate problems associated with errors in the light reading from ambient or stray light.

The device of the present invention has also been found to be particularly effective when used to provide a simple color-change indication of the refractometry of the liquid in which the multiple-bend sensor is immersed. A color-display device according to my invention has been illustrated in FIG. 9.

Figure 9:
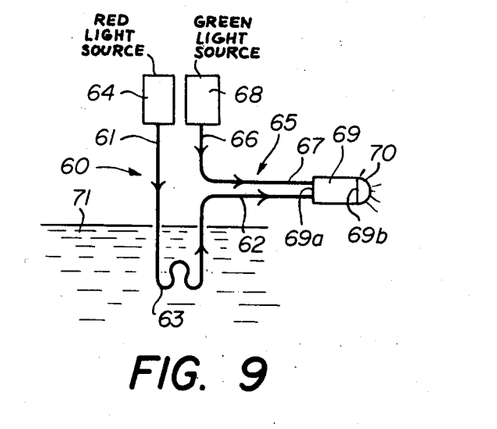
FIG. 9 is a schematic longitudinal sectional view illustrating a fourth embodiment.

In this sytem, a first light pipe or fiber-optic element 60 comprises an input section or stretch 61 and an output section or stretch 62 connected together by a triply curved sensing or intermediate section 63 in the form of an Ω. At least this intermediate section is adapted to be immersed in the liquid 71 to be tested.

The free end of the input section 61 is provided with a first illumination source 64 which directs a pencil of light of a first predetermined color into the end of this section. The source 64 may be constituted by a light-emitting diode or LED.

The system of FIG. 9 also comprises a second optical fiber or light pipe 65 having an input section or stretch 66 and an output section or stretch 67. This second fiber 65 is bent parallel to the output section 62 of the first fiber, so that the ends of these sections are connected by a mixer 69 which is also referred to as a randomizer. The second fiber 65 is located wholly externally of the liquid 71. The mixer can be an elongated light pipe of a cross-section greater than the total cross-sections of the optical fibers meeting it at its input end.

The input end of the second fiber 65 is provided with a second luminous source 68, e.g. another LED, delivering a pencil of light of a second color different from the first one to the second light pipe.

As noted, the output sections of the two optical fibers are connected to one end 69a of the mixer or randomizer 69 adapted to provide at its opposite end 69b a luminous display in the form of a beam of a color resulting from the mixture or superposition of the two input colors. The output end of 69b of the mixer 69 is provided with a conventional lens 70.

The operation of the system of FIG. 9 will be readily apparent. The sensitive part 63 of the first fiber 60 is immersed in the liquid 71 to be tested and the sources 64 and 68 inject the respective beams into the respective fibers 60 and 65 to provide a luminous display at the lens 70 which results from the blend of the constant color intensity from light pipe 65 and the variable color intensity from light pipe 62 which is a function of the index of refraction of the liquid. The color mix, therefore, will vary as a function of the index of refraction based upon the relationship of the intensities of the two beams.

The color-display device of FIG. 9, embodying another aspect of my present invention, may make use of other optical sensors than those incorporating the improvements described with reference to FIGS. 2–8. For example, the single-curve sensor of FIG. 1a may be used or the detector can be constituted by a prism or the like. The most important advantage of the system of FIG. 9 is that it provides a highly sensitive immediately visible color change to indicate even minute variations in the index of refraction of the liquid.

EXAMPLE 3

The device of FIG. 9 is used for testing the state of charge of a conventional lead-acid storage battery. The first light source 64 is constituted by a red LED fed with a constant current of 20 mA, while the second source 68 is a green LED also supplied with a constant current of 20 mA. The resulting beam at the display lens 70 shows a green-yellow color when the battery is completely charged (refractive index 1.378), a light yellow to yellow coloration with complete discharge (refractive index 1.348) and an orange-red coloration when the level of the electrolyte falls below the sensor 63 of the fiber 60. The device of FIG. 9 thus serves both as a level indicator and as a refractometer.

Figure 10:
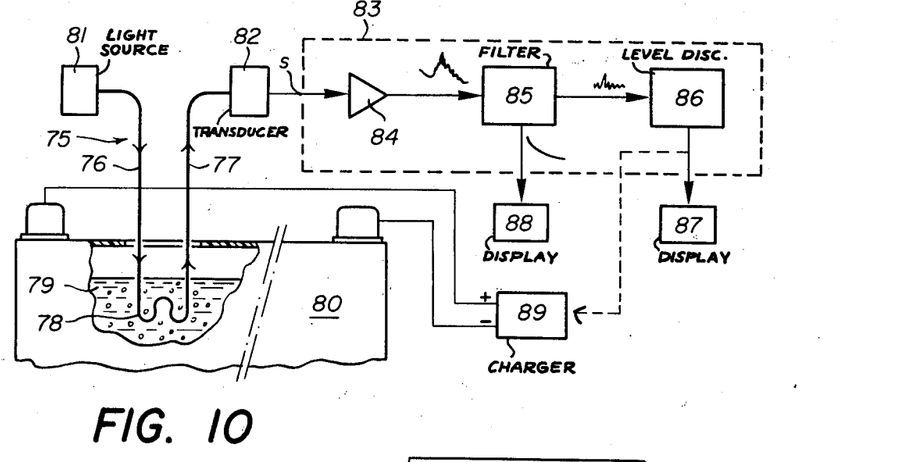
FIG. 10 is a schematic longitudinal sectional view illustrating a fifth embodiment.

The detector of the present invention can also be used for other purposes, e.g. in the system of FIG. 10 to detect the presence of gas bubbles within a liquid medium. This bubble-effect detector can be used for various purposes, for example, to detect bubbling in a storage battery during charge and hence as an overcharge-warning device, since overcharging results in the development of bubbles of gas within the electrolyte.

FIG. 10 shows just such a bubble detector serving as an overcharge-warning device and comprising a fiber-optical light pipe 75 having an input section or stretch 76, an ouput section or stretch 77 and a multiply curved Ω-shaped intermediate section 78 immersed in the electrolyte 79 of a lead-acid battery 80.

The free end of the input section 76 is provided with a light source 81 injecting a beam of light into this end of the fiber while the opposite end of the fiber is provided with a photoelectric transducer 82 whose output s is an electrical signal representing the light intensity emerging at the output section 77. The light source 81 can be constituted by a LED while the transducer 82 is constituted by a photodiode.

Figure 11:
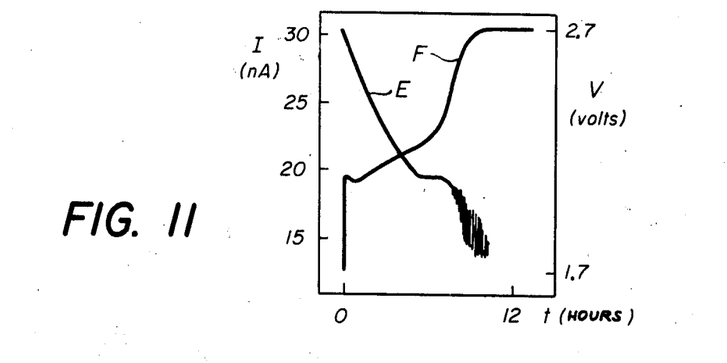
FIG. 11 is a diagram explaining the functioning of this fifth embodiment.

The variation of the electrical signal s as a function of the state of charge of the battery 80 is represented by the curve E in FIG. 11 in which signal current is plotted along one ordinate against time along the abscissa.

The other curve F of this diagram illustrates the charging as a function of time, i.e. the voltage V plotted along the other ordinate which rises during charging from about 1.7 volts to about 2.7 volts at the end of the charge. At the upper plateau gas bubbling results.

The curve E shows that the electrical signal s is constituted by a first component, slowly decreasing with time, characteristic of the index of refraction and thus the state of charge which levels off just before the end of charging at, say, 2.5 volts, and a second discontinuous component varying rapidly with time and representing the development of bubbling and the arrival of bubbles at the section 78 of the optical fiber 75. Each temporary contact of a bubble of gas with the sensing portion 78 appears to sharply increase the luminous transmission through the fiber 75.

The original signal s is applied to an electronic evaluating circuit 83 adapted to analyze the signal s to detect the appearance of the discontinuous second component representing gas evolutions.

The circuit 83 comprises a signal amplifier 84 directly connected to the output of the transducer 82 and amplifying the signal s. A filter 85 connected to the amplifier 84 separates the two components of the signal and passes only the high-frequency component which is applied to an integrator/level discriminator 86 connected to the output of the filter 85 for generating a warning signal when this second component, as integrated, passes a predetermined threshold value sufficient to prevent the generation of the warning signal by transient parasitic fluctuations which do not indicate the formation of gas bubbles on overcharge.

This signal is applied to a display device 87, e.g. a LED, and to the control circuit for the charger 89 to terminate the charging operation. The first component of the signal can be applied to a display 88 affording a continuous indication of the state of charge.

I claim:

1. A device for producing a luminous signal representing the refractive index of a liquid, comprising:
    an elongated light-conducting body having an input section, an intermediate section connected to said input section and an output section connected to said intermediate section, said intermediate section being curved so that the injection of light into said body at said input section results in a luminous signal at said output section corresponding to the refractive index of said liquid, said intermediate section having a plurality of successive curvatures alternately bent in opposite directions;
    a light source connected to said input section;
    means responsive to said signal at said output section; and
    an enclosure for said intermediate section placed at least over a region thereof to be immersed in said liquid and formed at least in part by a filter preventing particles in suspension in said liquid from depositing upon the curved intermediate section.

2. The device defined in claim 1 wherein said enclosure is formed with a window spanned by the filter material.

3. The device defined in claim 1 wherein said enclosure consists entirely of the filter material.

4. The device defined in claim 1, 2 or 3 wherein the filter is formed with a filter layer relatively distal from said intermediate section and serving as a prefilter, and a filter layer proximal to said intermediate curved section and serving as a final filter.

5. A device for displaying a characteristic of the refractive index of a liquid, comprising:
    an elongated light-conducting body having an input section, an intermediate section connected to said input section and an output section connected to said intermediate section, said intermediate section being curved so that the injection of light into said body at said input section results in a luminous signal at said output section varying with the refractive index of said liquid;
    a first light source of a first characteristic color at said input section for projecting light of said first color through said body;
    a second light source of a second characteristic color different from said first color;
    a light mixer connected to said output section and to said second light source for mixing light received from said output section and said second light source; and
    display means for displaying light formed in said mixer by the mixing of light from said body and said second light source.

6. The device defined in claim 5, further comprising a second elongated light-conducting body connecting said second light source with said mixer, the second body having an output section extending parallel to the output section of the first-mentioned body.

7. The device defined in claim 6 wherein said light sources are light-emitting diodes of different colors.

8. The device defined in claim 6 wherein said mixer comprises an elongated light-conducting member having a transverse cross-section substantially greater than the cross-sections of said first and second bodies, said sections of said first and second bodies joining one end of said member.

9. The device defined in claim 8 wherein the other end of said member is provided with a convergent lens.

10. The device defined in claim 5, 6, 7, 8 or 9 wherein said intermediate curved section has a profile comprising a plurality of curvatures arranged successively so as to be alternately bent in opposite directions to one another.

11. A device for detecting the presence of gas bubbles in a liquid which comprises:
    an elongated light-conducting body having an input section, an intermediate section connected to said input section and an output section connected to said intermediate section, said intermediate section being curved so that the injection of light into said body at said input section results in a luminous signal at said output section corresponding to the refractive index of said liquid:

a light source connected to said input section;

a photoelectric transducer connected to said output section for producing an electrical signal representing the light signal at said output section, said electrical signal having a high-frequency component upon the passage of bubbles along said intermediate section; and means connected to said transducer for separating said high-frequency component from another component for indicating the presence of gas bubbles in said liquid.

12. The device defined in claim 11 wherein said intermediate curved section has a profile comprising a plurality of curvatures arranged successively so as to be alternately bent in opposite directions to one another.

* * * * *